US007928057B2

(12) United States Patent
Ritter (10) Patent No.: US 7,928,057 B2
(45) Date of Patent: Apr. 19, 2011

(54) PEPTIDE FOR INHIBITION OF CALCINEURIN, NUCLEIC ACID, ANTIBODY, AND DIAGNOSTIC AND THERAPEUTIC METHODS OF USE

(75) Inventor: Oliver Ritter, Wuerzburg (DE)

(73) Assignee: Julius-Maximilians-Universitaet Wuerzburg, Wuerzburg (DE)

( * ) Notice: Subject to any disclaimer, the term of this patent is extended or adjusted under 35 U.S.C. 154(b) by 0 days.

(21) Appl. No.: 12/162,135

(22) PCT Filed: Jan. 25, 2007

(86) PCT No.: PCT/EP2007/000643
§ 371 (c)(1),
(2), (4) Date: Nov. 10, 2008

(87) PCT Pub. No.: WO2007/085455
PCT Pub. Date: Aug. 2, 2007

(65) Prior Publication Data
US 2009/0170765 A1    Jul. 2, 2009

(30) Foreign Application Priority Data
Jan. 27, 2006   (EP) .................................... 06090014

(51) Int. Cl.
A61K 38/04 (2006.01)
A61K 38/10 (2006.01)
A61K 38/16 (2006.01)
A61K 38/17 (2006.01)
C07K 7/08 (2006.01)
C07K 14/435 (2006.01)
C07K 16/18 (2006.01)
C12N 15/12 (2006.01)

(52) U.S. Cl. ...... 514/1.1; 514/16.4; 514/21.3; 514/21.5; 530/300; 530/324; 530/327; 530/387.9; 536/23.1; 536/23.5

(58) Field of Classification Search .................. None
See application file for complete search history.

(56) References Cited

U.S. PATENT DOCUMENTS
2003/0045679 A1   3/2003  Crawford
2003/0060399 A1   3/2003  Brophy et al.

FOREIGN PATENT DOCUMENTS
WO   WO 00/28011        5/2000
WO   WO 02/50097 A2     6/2002

OTHER PUBLICATIONS
Phillips, 2001, Journal of Pharmacy and Pharmacology 53:1169-1174.*
Verma et al., 1997, Nature 389:239-242.*
Anonymous, Internet Article, Calcineurin A Antibodies, Jan. 2005.

Aramburu, J., et al., "Affinity-Driven Peptide Selection of an NFAT Inhibitor More Selective than Cyclosporin A," Science, vol. 285, pp. 2129-2133, Sep. 1999.
Burkard, N., et al., "Targeted Proteolysis Sustains Calcineurin Activation," Circulation, vol. 111, pp. 1045-1053, 2005.
Cyert, M.S., "Regulation of Nuclear Localization during Signaling," J. of Biology Chemistry, vol. 276, No. 24, pp. 20805-20808, Jun. 2001.
Dolmetsch, R., et al., "Differential Activation of Transcription Factors Induced by $CA^{2+}$ Response Amplitude and Duration," Nature. vol. 386, pp. 855-858, Apr. 1997.
Fornerod, M., et al., "CRM1 is an Export Receptor for Leucine-Rich Nuclear Export Signals," Cell, vol. 90, pp. 1051-1060, Sep. 1997.
Frey, N., et al., Calsarcins, a Novel Family of Sarcomeric Calcineurin-Binding Proteins, Proc. Natl. Acad. Sci., pp. 14632-14637, Dec. 2000.
Gasiorowski, J., et al., "Mechanisms of Nuclear Transport and Interventions," Advanced Drug Delivery Reviews, vol. 55, pp. 703-716, 2003.
Hallhuber, M., et al., Inhibition of Nuclear Import of Calcineurin Prevents Myocardial Hypertrophy, Circulation Research, vol. 99, pp. 626-635, 2006.
Hallhuber, M., et al., "New Approach to Prevent Myocardial Hypertrophy," Future Cardiology, vol. 3, pp. 91-98, 2007.
Hogan, P.G., et al., "Modification by Nuclear Export?" Nature, vol. 398, pp. 200-201, 1999.
Jans, D., et al. "Nuclear Targeting Signal Recognition: A Key Control Point in Nuclear Transport?" BioEssays, vol. 22, pp. 532-544, 2000.
Kutay, U., et al., "Export of Importin α from the Nucleus is Mediated by a Specific Nuclear Transport Factor," Cells, vol. 90, pp. 1061-1071, Sep. 1997.
McKinsey, T., et al., Signal-Dependent Nuclear Export of a Histone Deacetylase Regulates Muscle Differentiation, Nature, vol. 408, pp. 106-111, Nov. 2000.
Pemberton, L., et al., "Mechanisms of Receptor-Mediated Nuclear Import and Nuclear Export," Traffic, vol. 6, pp. 187-198, 2005.
Ritter, O., et al., "Calcineurin in Human Heart Hypertrophy," Circulation, vol. 105, pp. 2265-2269, 2002.
Ritter, O., et al. "$AT_2$-Receptor Activation Regulates Myocardial eNOS Expression Via the Calcineurin-NF-AT Pathway," FASEB Journal, vol. 17, pp. 283-285, 2003.
Shibasaki, F., et al., "Role of Kinases and the Phosphatase Calcineurin in the Nuclear Shutting of Transcription Factor NF-AT4," Nature, vol. 382, pp. 370-373, Jul. 1996.
Timmerman, L., et al., "Rapid Shutting of NF-AT in Discrimination of $CA^{2+}$ Signals and Immunosuppression," Nature, vol. 383, pp. 837-840, 1996.

(Continued)

Primary Examiner — Elizabeth C. Kemmerer
(74) Attorney, Agent, or Firm — Vedder Price P.C.; Ajay A. Jagtiani (57) ABSTRACT

The present invention relates to a method for diagnosing susceptibility for a myocardial and/or immunological disorder, a kit and a therapeutic agent comprising a peptide of SEQ ID NO: 1 or 2 and uses thereof.

12 Claims, 9 Drawing Sheets

OTHER PUBLICATIONS

Wilkins, B., et al., "Calcineurin/NFAT Coupling Participates in Pathological, but not Physiological, Cardiac Hypertrophy," Circulation Research vol. 94, pp. 110-118, 2004.

Wu, H., et al., "Critical Role of Calpain-Mediated Cleavage of Calcineurin in Excitotoxic Neurodegeneration," J. of Biology Chemistry, vol. 279, pp. 4929-4940, 2004.

Zhu, J., et al., "NF-AT Activation Requires Suppression of Crm1-Dependent Export by Calcineurin," Nature, vol. 398, pp. 256-260, 1999.

Zou, Y., et al., "Isopreternol Activates Extracellular Signal-Regulated Protein Kinases in Cardiomyocytes through Calcineurin," Circulation, vol. 104, pp. 102-108, 2001.

* cited by examiner

```
                        SEQUENCE LISTING

<160> NUMBER OF SEQ ID NOS: 10

<210> SEQ ID NO 1
<211> LENGTH: 27
<212> TYPE: PRT
<213> ORGANISM: Artificial Sequence
<220> FEATURE:
<223> OTHER INFORMATION: nuclear localisation signal and membrane anker

<400> SEQUENCE: 1

Ala Ala Val Ala Leu Leu Pro Ala Val Leu Leu Ala Leu Leu Ala Lys
1               5                   10                  15

Gln Glu Cys Lys Ile Lys Tyr Ser Glu Arg Val
            20                  25

<210> SEQ ID NO 2
<211> LENGTH: 12
<212> TYPE: PRT
<213> ORGANISM: Artificial Sequence
<220> FEATURE:
<223> OTHER INFORMATION: nuclear localisation signal

<400> SEQUENCE: 2

Lys Gln Glu Cys Lys Ile Lys Tyr Ser Glu Arg Val
1               5                   10

<210> SEQ ID NO 3
<211> LENGTH: 27
<212> TYPE: PRT
<213> ORGANISM: Artificial Sequence
<220> FEATURE:
<223> OTHER INFORMATION: control peptide and membrane anker

<400> SEQUENCE: 3

Ala Ala Val Ala Leu Leu Pro Ala Val Leu Leu Ala Leu Leu Ala Ala
1               5                   10                  15

Gln Glu Cys Ala Ile Ala Tyr Ser Glu Tyr Val
            20                  25

<210> SEQ ID NO 4
<211> LENGTH: 15
<212> TYPE: PRT
<213> ORGANISM: Artificial Sequence
```

```
<220> FEATURE:
<223> OTHER INFORMATION: alternative membrane anker

<400> SEQUENCE: 4

Ala Ala Val Ala Leu Leu Pro Ala Val Leu Ala Ala Leu Ala Ala
 1               5                  10                  15

<210> SEQ ID NO 5
<211> LENGTH: 27
<212> TYPE: PRT
<213> ORGANISM: Artificial Sequence
<220> FEATURE:
<223> OTHER INFORMATION: alternative nucl loc signal plus membrane anker

<400> SEQUENCE: 5

Ala Ala Val Ala Leu Leu Pro Ala Val Leu Ala Ala Leu Ala Ala Lys
 1               5                  10                  15

Gln Glu Cys Lys Ile Lys Tyr Ser Glu Arg Val
            20                  25

<210> SEQ ID NO 6
<211> LENGTH: 27
<212> TYPE: PRT
<213> ORGANISM: Artificial Sequence
<220> FEATURE:
<223> OTHER INFORMATION: alternative nucl loc signal plus membrane anker
      II

<400> SEQUENCE: 6

Ala Ala Val Ala Leu Leu Pro Ala Val Leu Ala Ala Leu Ala Ala Lys
 1               5                  10                  15

Gln Glu Ala Lys Ile Lys Tyr Ser Glu Arg Val
            20                  25

<210> SEQ ID NO 7
<211> LENGTH: 27
<212> TYPE: PRT
<213> ORGANISM: Artificial Sequence
<220> FEATURE:
<223> OTHER INFORMATION: alternative nucl loc signal plus membrane anker
      III

<400> SEQUENCE: 7

Ala Ala Val Ala Leu Leu Pro Ala Val Leu Ala Ala Leu Ala Ala Lys
 1               5                  10                  15

Gln Glu Cys Lys Ile Lys Tyr Ala Glu Arg Val
            20                  25

<210> SEQ ID NO 8
<211> LENGTH: 27
<212> TYPE: PRT
<213> ORGANISM: Artificial Sequence
<220> FEATURE:
<223> OTHER INFORMATION: alternative nucl loc signal plus membrane anker
      IV

<400> SEQUENCE: 8

Ala Ala Val Ala Leu Leu Pro Ala Val Leu Ala Ala Leu Ala Ala Lys
 1               5                  10                  15

Gln Glu Ala Lys Ile Lys Tyr Ala Glu Arg Val
            20                  25

<210> SEQ ID NO 9
<211> LENGTH: 27
<212> TYPE: PRT
<213> ORGANISM: Artificial Sequence
```

```
<220> FEATURE:
<223> OTHER INFORMATION: alternative nucl loc signal plus membrane anker
      V

<400> SEQUENCE: 9

Ala Ala Val Ala Leu Leu Pro Ala Val Leu Ala Ala Leu Ala Ala Lys
  1               5                  10                  15

Ala Glu Cys Lys Ile Lys Tyr Ser Glu Arg Val
             20                  25

<210> SEQ ID NO 10
<211> LENGTH: 27
<212> TYPE: PRT
<213> ORGANISM: Artificial Sequence
<220> FEATURE:
<223> OTHER INFORMATION: alternative nucl loc signal plus membrane anker
      VI

<400> SEQUENCE: 10

Ala Ala Val Ala Leu Leu Pro Ala Val Leu Ala Ala Leu Ala Ala Lys
  1               5                  10                  15

Ala Glu Ala Lys Ile Lys Tyr Ser Glu Arg Val
             20                  25
```

PEPTIDE FOR INHIBITION OF CALCINEURIN, NUCLEIC ACID, ANTIBODY, AND DIAGNOSTIC AND THERAPEUTIC METHODS OF USE

FIELD OF THE INVENTION

The present invention relates to a method for diagnosing susceptibility for a myocardial and/or immunological disorder, a kit, an antibody and a therapeutic agent comprising a peptide of SEQ ID NO: 1, 2, 5-10 and uses thereof.

BACKGROUND OF THE INVENTION

The movement of proteins over ~40 kDa into and out of the nucleus is governed by the nuclear pore complex (NPC), a multi subunit structure embedded in the nuclear envelope (Jans et al., 2000). Transcription factors and enzymes that regulate the activity of these proteins are shuttled across the nuclear envelope by proteins that recognize nuclear localization signals/sequences (NLS) and nuclear export signals (NES). Positively charged NLSs are bound by importins α and/or β—also known as karyopherins—which tether cargo to the cytosolic face of the nuclear pore complex and facilitate translocation of proteins into the nucleus. The CRM1 protein, also referred to as exportin, mediates the transfer of proteins out of the nucleus (Fornerod et al., 1997), although CRM1-independent mechanisms for nuclear export exist (Kutay et al., 1997). The ability of nuclear import and export machinery to access a NLS or NES is often dictated by signalling events that lead to the exposure or masking of these regulatory sequences (Cyert, 2001). This may occur through direct modification of the target protein or via modification of an associated factor.

The signalling cascade of calcineurin (CnA) and the nuclear factor of activated T cells (NF-ATc) is a crucial transducer of cellular function. NF-ATc is an ubiquitous transcription factor but has particular relevance in cytokine expression and the development of pathologic myocardial hypertrophy. The formation of complexes between transcription factors and DNA is crucial for the transcriptional process. Therefore, the time that transcription factors remain nuclear is a major determinant for transcriptional activity. It was shown that that in addition to the transcription factor NF-ATc, the phosphatase calcineurin is also translocated to the nucleus (Burkhard et al., 2005; Frey et al., 2000; Zou et al., 2001; Shibasaki et al., 1996). Calcineurin is therefore not only responsible for dephosphorylating NF-ATc, thus enabling its nuclear import; its presence in the nucleus is also significant in ensuring the full transcriptional activity of NF-ATc (Zhu et al., 1999). The traditional understanding of calcineurin activation via sustained high $Ca^{2+}$-levels (Timmerman et al., 1996; Dolmetsch et al., 1997) was advanced by findings of the inventor that calcineurin is activated by proteolysis of the C-terminal auto-inhibitory domain, which leads to a constitutively nuclear translocation of calcineurin (Burkhard et al., 2005).

Calcineurin is known to suppress the immune system, and various pharmaceutical compositions are available from commercial sources. Calcineurin inhibitors belong to the group of cyclosporine, tacrolimus (Protopic®, Prograf®) and pimecrolimus. Indications are psoriasis, atopic dermatitis, rheumatism and allergies, to name a few.

US patent application No. 2003/0045679 A1 to Crawford describes compositions which are useful for inhibiting and potentiating the activity of cellular calcineurin. These compositions include peptides, peptide analogs and whole proteins. They can be used to treat calcineurin related pathologies such as cardiac, brain, immune system and developmental abnormalities.

All known calcineurin inhibitors show strong side effects like high blood pressure, renal disorders and viral and bacterial infections. The later two are due to their general immunosuppressive properties. Thus there is a still existing need for a pharmaceutical composition for the treatment of calcineurin related disorders, like myocardial disorders, psoriasis, rheumatism, immune reactions and suppression, e.g. graft versus host reaction and transplant rejection; allergies, asthma, in particular cardiac asthma, bronchial asthma and allergic asthma.

The solution to this problem is achieved by providing the embodiments characterized by the claims, and described further below.

SUMMARY OF THE INVENTION

The present invention is directed to a method for diagnosing susceptibility for a myocardial and/or immunological disorder comprising the steps of (a) providing a test sample comprising at least one cell; (b) contacting the cell with a peptide of SEQ ID NO: 1, 2, 5-10; (c) determining an interaction between the peptide of SEQ ID NO: 1 or 2 and cellular calcineurin; wherein a primarily nuclear localization of a complex comprising calcineurin and the peptide of SEQ ID NO: 1, 2, 5-10 indicates susceptibility for a myocardial and/or immunological disorder.

Further, the present invention is directed to a kit comprising the peptide of SEQ ID NO: 1, 2, 5-10 for diagnosing a myocardial and/or immunological disorder.

The present invention also concerns a therapeutic agent comprising the peptide of SEQ ID NO: 1, 2, 5-10, a nucleic acid which encodes the peptide of SEQ ID NO: 1, 2, 5-10 or a peptide of at least 90% identity of the peptide of SEQ ID NO: 1, 2, 5-10. The peptide inhibits substantially the translocation, transport or shuffling of calcineurin and its derivates from the cytoplasm to the nucleus of a cell.

Further the present invention is directed to an antibody against the peptide of SEQ ID NO: 1, 2, 5-10.

Moreover, the present invention is also directed to the use of the peptide of SEQ ID NO: 1, 2, 5-10 for manufacturing a therapeutic agent for prophylactic and/or therapeutic treatment of a myocardial and/or immunological disorder.

BRIEF DESCRIPTION OF THE DRAWINGS

FIG. 5 shows functional consequences of inhibition of calcineurin (CnA) nuclear import. Neonatal rat cardiomyocytes were incubated with a peptide mimicking the NLS sequence of CnA (SEQ ID NO:2) and stimulated with Ang II (100 μM). The peptide saturated CnA/importin β1 binding capacity. Nuclear import of CnA was therefore prevented. Control experiments were performed with a non-sense peptide SEQ ID NO: 3).

FIG. 5A top shows that phosphatase activity of CnA was not influenced by the synthetic NLS peptide (SEQ ID NO: 2) as measured using a specific phosphor substrate of CnA.

FIG. 5A bottom shows that transcriptional activity of the calcineurin/NF-ATc complex was suppressed by the inhibitory NLS peptide (SEQ ID NO: 2). Transcriptional activity was assessed with a NF-ATc luciferase reporter plasmid.

DETAILED DESCRIPTION OF THE INVENTION

The inventor has surprisingly found that a peptide which mimics the nuclear localization signal of calcineurin (SEQ ID NO: 2) successfully prevents the translocation of calcineurin from the cellular cytoplasm to the nucleus. Without intending to be bound by any theory, it is believed that the NLS peptide (SEQ ID NO: 2) binds to importin, thereby preventing complex formation between calcineurin and importin. However, complex formation between calcineurin and importin is necessary for transporting calcineurin to the nucleus, where calcineurin together with NF-ATc then act as activated transcription factor due to the constant presence of calcineurin. The NLS peptide (SEQ ID NO: 2) efficiently inhibits complex formation and thereby blocks entry of calcineurin into the nucleus. It is further believed that that the auto-inhibitory domain (AID) not only blocks the catalytical activity of calcineurin but also masks the nuclear localization signal. Removal of the AID via a conformational change in calcineurin following $Ca^{2+}$ activation or by proteolysis of the auto-inhibitory domain leads to exposure of the nuclear localization signal and resultant nuclear translocation of calcineurin.

Sequences with SEQ ID NO: 5-10 (see section Examples) also proved to behave similar like SEQ ID NO: 1 and can be equally used in the present invention.

Myocardial disorders and immunological disorder are associated with altered transcription patterns of NF-ATc downstream targets. Therefore, the NLS peptide may be used as a diagnostic tool for assessing the susceptibility for a myocardial and/or immunological disorder.

In a first aspect, the present invention is directed to a method for diagnosing susceptibility for a myocardial and/or immunological disorder comprising the steps of:
a) providing a test sample comprising at least one cell;
b) contacting the cell with a peptide of SEQ ID NO: 1, 2, 5-10;
c) determining an interaction between the peptide of SEQ ID NO: 1, 2, 5-10 and cellular calcineurin;
wherein a primarily nuclear localization of a complex comprising calcineurin and the peptide of SEQ ID NO: 1, 2, 5-10 indicates susceptibility for a myocardial and/or immunological disorder.

As used herein the term susceptibility means predisposition or likelihood for the development of a myocardial and/or immunological disorder. The term disorder means a dysfunction, a malfunction, a disease or a medical condition. The term peptide includes linear peptides, cyclic peptides and peptide analogs, derivates and salts thereof. Cyclic peptides are particularly preferred. Peptides forming a cyclic peptide may be closed head to tail, head to one of the side chains or tail to one of the side chains. Any modification can be employed as long as the peptide retains its ability to prevent entry of calcineurin into the nucleus of a cell. The peptides of the present invention can be incorporated in a structure comprising more amino acids, and the peptides comprise preferably about 60 amino acids, more preferred about 30 to 40 amino acids, most preferred about 20 to 30 amino acids.

The test sample can be derived from an animal, in particular a mammal, preferably from a human, more preferably from a patient who is suspected to be susceptible of a myocardial and/or immunological disorder.

Likewise, SEQ ID NO: 1, 2, 5-10 can be used for a method for diagnosing further calcineurin related disorders, like myocardial disorders, immunological disorders, psoriasis, rheumatism, immune reactions and suppression, e.g. graft versus host reaction and transplant rejection; allergies, asthma, in particular cardiac asthma, bronchial asthma and allergic asthma.

In a preferred embodiment the peptide of SEQ ID NO: 1, 2, 5-10 is chemically, biologically and/or physically labeled. Examples for labeling peptides are dyes, like streptavidin-biotin labeling, fluorescent labeling, labeling by antibodies and radioactive labeling.

In a further preferred embodiment the myocardial disorder is selected from the group consisting of hypertrophic cardiomyopathy, in particular hypertrophic obstructive cardiomyophathy, hypertensive cardiomyopathy, ischemic cardiomyopathy, dilated cardiomyopathy, aortic stenosis and heart attack. The immunological disorder is selected from the group consisting of transplant rejection and immune suppression. It is also possible to prevent restenosis after stent implantation by means of the NLS peptide of the present invention.

In a particularly preferred embodiment the disorder is a T-cell associated disorder. Specific examples for T-cell associated disorders are rheumatoid arthritis and forms thereof, psoriasis, psoriasis arthritis, systemic lupus erythematodes, vasculitis, other mixed connective tissue diseases, Sjögren syndrome, uveitis, inflammatory bowl diseases like Colitis ulcerosa and Morbus Crohn, intrinsic/extrinsic asthma, graft versus host reaction and transplant rejection (prevention of organ rejection and treatment of chronic rejection)

Also diagnostic purposes with respect to T-cells are enclosed. The peptide may be used in a diagnostic kit to test activation status of T-cells from patients. This may be used to monitor disease progress or therapeutic success in e.g. immunosuppressed patients with transplanted organs.

In a second aspect the invention provides a kit comprising the peptide of SEQ ID NO: 1, 2, 5-10 for diagnosing susceptibility for a myocardial and/or immunological disorder. Likewise, SEQ ID NO: 1, 2, 5-10 can be used for a kit for diagnosing further calcineurin related disorders, like myocardial disorders, immunological disorders, psoriasis, rheumatism, immune reactions and suppression, e.g. graft versus host reaction and transplant rejection; allergies, asthma, in particular cardiac asthma, bronchial asthma and allergic asthma.

In another aspect the present invention concerns a therapeutic agent comprising the peptide of SEQ ID NO: 1, 2, 5-10 and a therapeutic agent comprising a nucleic acid which encodes the peptide of SEQ ID NO: 1, 2, 5-10.

The term nucleic acid, as used herein, includes DNA molecules, like cDNA and genomic DNA, RNA molecules, like mRNA, analogs of DNA and RNA which are generated by nucleotide analogs and derivates, fragments and homologs thereof. The nucleic acid can be single stranded or double stranded, however double stranded DNA molecules are preferred.

In another aspect, the present invention covers a therapeutic agent comprising a peptide of at least 90%, preferably at least 95%, more preferred at least 98%, still more preferred 100% identity of the peptide of SEQ ID NO: 1, 2, 5-10; wherein the peptide substantially inhibits the translocation of calcineurin from the cytoplasm to the nucleus of a cell. Conserved amino acid substitutions are covered by the present disclosure. The peptide of SEQ ID NO: 2 comprises three lysine amino acids (K) at positions 1, 5 and 7. When all lysine residues (K) are substituted by alanine (A) the peptides does no longer inhibit entry of calcineurin to the nucleus. However individual lysine residues may be substituted as long as the peptide prevents it ability to block the translocation of calcineurin from the cytoplasm to the nucleus of a cell.

In a preferred embodiment the therapeutic agent further comprises a pharmaceutically acceptable carrier, like fillers and excipients. Various application forms of the peptides are possible. Cremes and ointments can be applied topically. In stent technology, the peptide can be used to cover a stent, which is then implanted to a patient in need thereof. Coronary stents are particularly preferred. Also intravascular pumps, in particular mini pumps can be used for delivery of the peptide to a patient.

In a further aspect, the invention is directed to an antibody against the peptide of SEQ ID NO: 1, 2, 5-10.

In another aspect, the present invention covers the use of the peptide of SEQ ID NO: 1, 2, 5-10 for manufacturing a therapeutic agent for prophylactic and/or therapeutic treatment of a myocardial and/or immunological disorder.

In a preferred embodiment the myocardial disorder is selected from the group consisting of hypertrophic cardiomyopathy, in particular hypertrophic obstructive cardiomyophathy, hypertensive cardiomyopathy, ischemic cardiomyopathy, dilated cardiomyopathy, aortic stenosis and heart attack. The immunological disorder is selected from the group consisting of a transplant rejection and immune suppression.

In yet another aspect the present invention is directed to the use of the peptide of SEQ ID NO: 1, 2, 5-10 for manufacturing a therapeutic agent for prophylactic and/or therapeutic treatment of calcineurin related disorders, like myocardial disorders, immunological disorders, psoriasis, rheumatism, immune reactions and suppression, e.g. graft versus host reaction and transplant rejection; allergies, asthma, in particular cardiac asthma, bronchial asthma and allergic asthma.

A more complete understanding of the present invention can be obtained by reference to the following examples, which are provided for the purpose of illustration only and are not intended to limit the scope of the invention.

EXAMPLES

A) Material and Methods

The following materials and methods were employed:
Cell Culture

Neonatal rat cardiomyocytes of Wistar rats were isolated as described previously (Ritter et al., 2003). Cells were resuspended in minimum essential medium/1% FCS. After pre-plating, the cardiomyocyte containing supernatant was recovered, and cells were plated in minimum essential medium on 6-well plates at a density of $1 \times 10^6$ cells per well. The medium for cardiomyocytes contained 5-bromo-2'-deoxyuridine (0.1 mmol/L) to suppress fibroblast growth. Fibroblast contamination of cardiomyocyte cultures was between 4% and 7% as regularly determined by immunohistochemical staining for troponin T. HeLa cells were grown in DMEM/5% FCS (Sigma). 48 hours after preparation, cells were stimulated with 10 nmol/L angiotensin II (Ang II). Cells were harvested 24 hours after stimulation. Concentrations were as follows: Ang II: 10 µM, calpeptin: 10 µM, NLS peptide and control peptide: 1 µM, respectively.

Calcineurin (CnA) Activity

NF-ATc reporter plasmid comprised the Il-2 promoter followed by luciferase. Luciferase activity was determined according to the manufacturer's protocol (Promega). CnA phosphatase activity was determined using a commercial kit (CnA kit assay, Biomol) that measures effect on a specific CnA phosphosubstrate. Free PO₄ was indicated by a malachite green dye. The use of this kit has been described previously (Ritter et al., 2002).

Plasmids

Epitope-tagged derivatives of calcineurin Aβ containing amino-terminal EGFP were generated using the mammalian expression vector pEGFP-C3 (BD Bioscience Clontech). For cloning of calcineurin mutants the mammalian expression vector pCMV-Sport6 containing the directionally cloned cDNA of human calcineurin Aβ was used (Invitrogen). The following mutants have been amplified by PCR, digested with XbaI and XhoI and cloned into the XbaI and XhoI sites of the described plasmid: CnAβ(full), CnAβ 1-415, CnAβ 1-425, CnAβ 1-445, CnAβ 1-465, CnAβ 1-485 and CnAβ 171-190. For these truncated mutants different reverse oligonucleotides were designed with subsequent N-terminal binding sites. The forward primer, binding at the N-terminus of calcineurin, was identical for each plasmid apart from the CnA (171-190) mutant. For this derivative primers are bound upstream of aa 171 and downstream of aa 190, respectively. Two internal mutants CnAβ(Δ420-434) and CnAβ(Δ420-445) were cloned into the XbaI and XhoI sites of pEGFP-C3 using a two step strategy. For deleting the short areas from aa 420 to 434 and from aa 420 to 445 two fragments have been amplified. After ligation of these two fragments the resulting whole fragment was cloned into the XbaI and XhoI sites of pEGFP-C3. FLAG-tagged calcineurin derivatives were kindly provided by the group of Ludwig Neyses (Divison of Cardiology, The University of Manchester).

Immunofluorescence and Immunoprecipitation

The subcellular distribution of calcineurin was determined by immunofluorescence stainings. The primary antibodies used in fluorescence staining are described elsewhere (Burkhard et al., 2005). Secondary antibodies were Cy-3-labeled sheep anti-rabbit IgG or Cy2-conjugated mouse anti-goat IgG (Jackson Laboratories).

B) Results

The inventor's group demonstrated that posttranslational modification, specifically proteolysis of the auto-inhibitory domain (AID) of calcineurin leads to its activation and strong nuclear translocation (Burkhard et al., 2005). The calpain mediated cleavage of the c-terminal AID and the causative link to myocardial hypertrophy was demonstrated in human myocardial tissue.

In this invention the inventor demonstrates the prominent nuclear translocation of CnA in different animal models of diseased myocardium. In wild-type mice a predominantly cytosolic distribution of CnA was observed, whereas in mice that underwent aortic banding or myocardial infarction a strong nuclear localization of CnA in the hypertrophied myocardium was observed.

This is consistent with observations of nuclear import of calcineurin in cell culture models (Burkhard et al., 2005; Frey et al., 2000; Zou et al., 2001; Zhu et al., 1999). However, the role of calcineurin within the nucleus was not been investigated before and the precise mechanism leading to nuclear import and export remains unclear.

Reversible Nuclear Localization of Calcineurin after Angiotensin Stimulation

To assess whether CnA import into the nucleus is a chronic phenomenon or an acute response the inventor investigated the time course of CnA shuttling. A GFP tagged calcineurin plasmid encoding full length CnAβ was transfected into neonatal rat cardiomyocytes. Cells were stimulated with Ang II at 10 μM. Confocal microscopy revealed onset of nuclear translocation of calcineurin after 2 h. After 4 h of Ang II stimulation CnA was predominantly nuclear. After 6 h maximum of intensity of the GFP-calcineurin signal was in the nucleus. Similarly, 2 h after removal of Ang II from the medium there was a homogenous distribution of CnA in the cytosol and the nucleus and after 4 h there was perinuclear localization of CnA. 6 h after removal of the stimulus calcineurin localised completely in the cytosol again. To prevent CnA from calpain mediated proteolysis, which would cause constitutive activation of CnA and therefore persistent nuclear translocation, all experiments where performed in the presence of a membrane permeable calpain inhibitor (Burkhard et al., 2005). Calcineurin is very sensitive to pathological stimuli in cardiomyocytes and is able to induce a response within a few hours after the initial stimulation.

Construction of NLS Peptide Mutants

Figure 1:
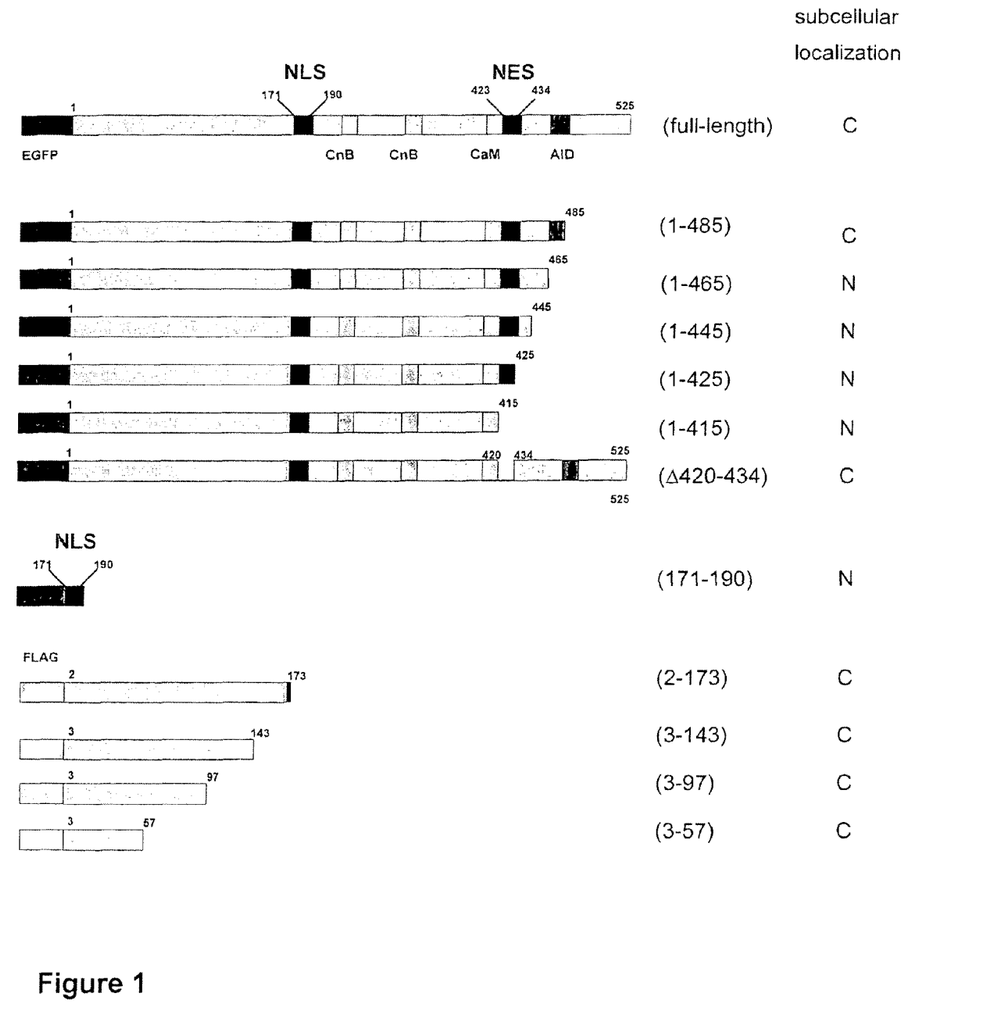
FIG. 1 shows the identification of a nuclear localization signal (NLS) in calcineurin (CnA). A schematic drawing of green fluorescent protein (GFP)- and FLAG-tagged CnA deletion mutants is given. The subcellular localization is indicated (c=primarily cytoplasmatic; n=primarily nuclear). NLS=nuclear localization signal; NES=nuclear export sequence; CnB=calcineurin B binding domain; CaM=calmodulin binding domain; AID=auto-inhibitory domain; numbers correspond to CnAβ amino acid sequence; EGFP and FLAG indicate tags.

The transport of proteins into the nucleus relies on nuclear localization signal/sequences (NLS) which are bound by importins; the complex of cargo protein and importin is then transported into the nucleus. To define the regions of calcineurin that are required for nuclear import different GFP- or FLAG-tagged calcineurin deletion mutants (FIG. 1) were screened to assess those that entered the nucleus and those that remained cytosolic. In general, deletion of the auto-inhibitory domain led to nuclear translocation and deletion of the region starting amino acid 173 (within the putative NLS) prevented calcineurin from entering the nucleus. The mutants 2-173 and 3-143 may have reduced catalytic phosphatase activity as the catalytic subunit of CnA extends to amino acid 333. Therefore failure to translocate may in theory be a result of decreased phosphatase activity. Previous work however has demonstrated that catalytically inactive CnA mutants are also translocated into the nucleus (Shibasaki et al., 1996). Sequence comparisons with known NLS of other proteins enabled further delineation of the putative NLS region to the sequence 171-190. Fusion of this 171-190 fragment to the GFP backbone resulted in translocation of the GFP/NLS fusion protein into the nucleus, whereas the pure GFP backbone remained cytosolic. Whilst full length CnA resides in the cytosol, it was translocated into the nucleus after Ang II stimulation due to removal of the auto-inhibitory domain from the catalytic subunit and probably from the putative NLS. In contrast, deletion mutants 2-173 and 3-143 which both lacked the putative NLS remained exclusively cytosolic despite Ang 11 stimulation.

Interaction Between Calcineurin Mutants and Importin

Figure 2:
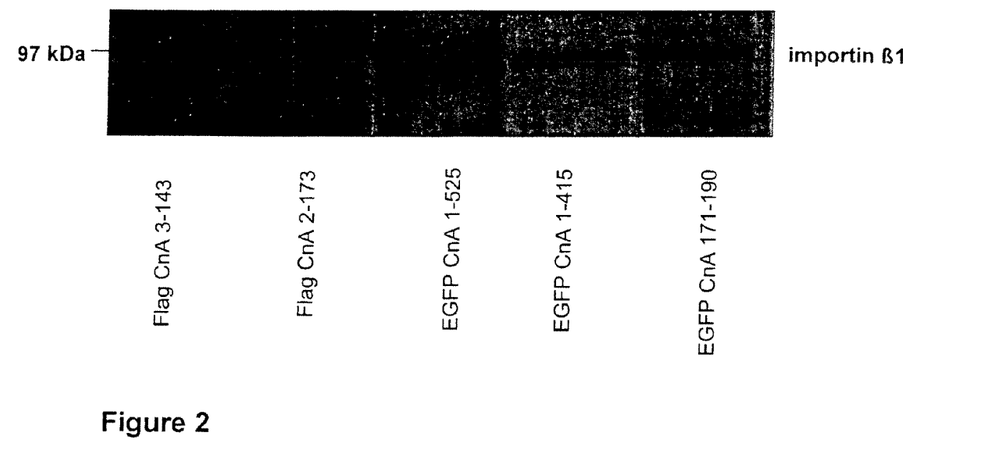
FIG. 2 shows interactions of calcineurin (CnA) with importin β1. Various deletion mutants were transfected into HeLa cells. Immunoprecipitation of GFP-tagged full length CnA and GFP-NLS fusion protein was performed with a GFP-antibody; the FLAG-tagged CnA 2-173 and CnA 3-143 mutants were precipitated with a FLAG-antibody. Immunodetection was performed with an importin β1 antibody. Full length calcineurin interacted with importin β1 as demonstrated by co-immunoprecipitation whereas the truncated CnA-mutants, lacking the NLS, did not co-immunoprecipitate with importin.

Importin β1 has been shown to bind the NLS of different cargo proteins (Pemberton et al., 2005). Interactions between CnA mutants and importin β1 were assessed to determine whether the functionally defined NLS physically interacts with importin β1. As demonstrated by co-immunoprecipitation experiments importin β1 displayed good affinity for full length calcineurin and also the deletion mutant CnA 1-415. Specifically, the interaction domain was mapped to the region 171-190 as evidenced by the ability of a fusion protein consisting of GFP and the 171-190 fragment to co-precipitate importin 131. However, both deletion mutants 1-173 and 1-143 completely abolished the interaction between importin β1 and CnA. These data indicate that the NLS identified by functional analyses also mediate interactions between importin β1 and calcineurin (FIG. 2).

Peptide Competition Assay

Figure 3:
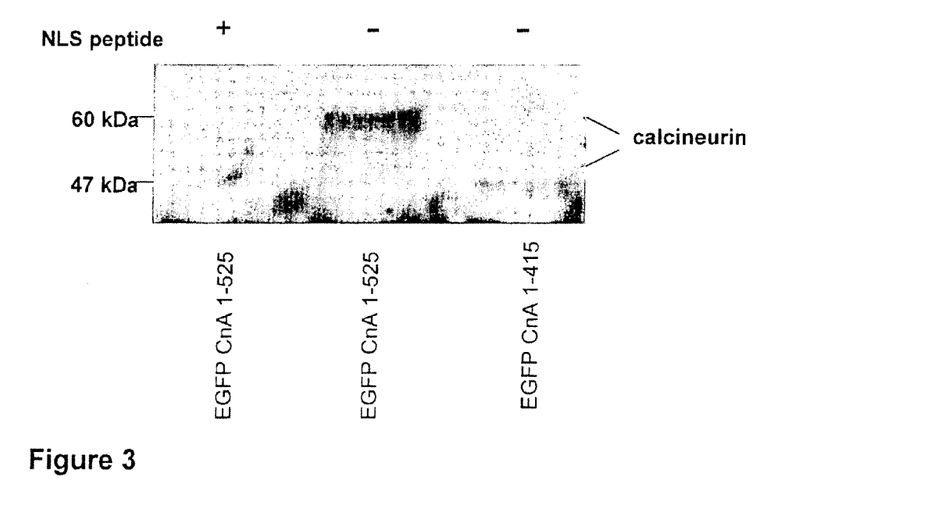
FIG. 3 shows the results of HeLa cells, which were transfected with the indicated GFP-tagged CnA mutants. Immunoprecipitation of the CnA/importin complexes was performed with importin β1 antibodies, detection with a GFP antibody. Addition of the NLS peptide (SEQ ID NO: 2) abrogated calcineurin interaction with importin β1.

To demonstrate further that the identified NLS in CnA is essential for the nuclear import of calcineurin, a peptide competition assay to prevent importin β1/CnA binding was used. A peptide with the putative NLS sequence of calcineurin (AAVALLPAVLLALLAKQECKIKYSERV—SEQ ID NO:

1) was synthesised and added to the medium (the first 15 letters give N-terminal extension to increase membrane permeability, NLS sequence is underlined). However, the peptide facilitating membrane permeability is not critical, and an alternative membrane anker, harbouring two alanine residues instead of leucine residues at positions 11 and 14, respectively, can also be used (AAVALLPAVLAALAA—SEQ ID NO: 4). In control experiments a non sense peptide (AAVALLPAVLLALLAAQECAIAYSEYV—SEQ ID NO: 3) was used. Addition of the synthetic NLS peptide saturated the binding domain of importin β1 for CnA and therefore prevented CnA binding to importin β1. Inhibition of this interaction suppressed calcineurin nuclear import. The noninhibitory control peptide did not interfere with the calcineurin/importin binding; accordingly, nuclear translocation of CnA was not inhibited. Also the NLS peptide abrogated the interaction of calcineurin and importin β1 as demonstrated in co-immunoprecipitation assays (FIG. 3).

Nuclear Export Control Sequences

To identify sequences in CnA that control nuclear export serial carboxyterminal truncation mutants with an N-terminal GFP tag of CnA were generated and examined by confocal fluorescence microscopy. Experiments were performed in the presence of a calpain inhibitor to prevent calpain induced cleavage of the auto-inhibitory domain (AID) and to ensure functional integrity of calcineurin. Cells were stimulated with Ang II for 12 h to achieve nuclear entry of CnA, subsequently the stimulus was removed to promote nuclear export. Full-length CnA (amino acids 1-524) was re-localized exclusively to the cytosol of transfected cardiomyocytes after removal of the stimulus. An extended deletion variant (1-415) was not able to leave the nucleus any more.

These results demonstrated that sequences in the region c-terminal to amino acid 415 regulate nuclear export. Consistent with these findings and sequence comparisons with known NES sites, a CnA mutant lacking amino acids 420-434 remained exclusively nuclear after removal of the stimuli. Inhibition of calpain did not influence this result as the calpain cleavage site (at 424) was deleted in this mutation variant.

Figure 4:
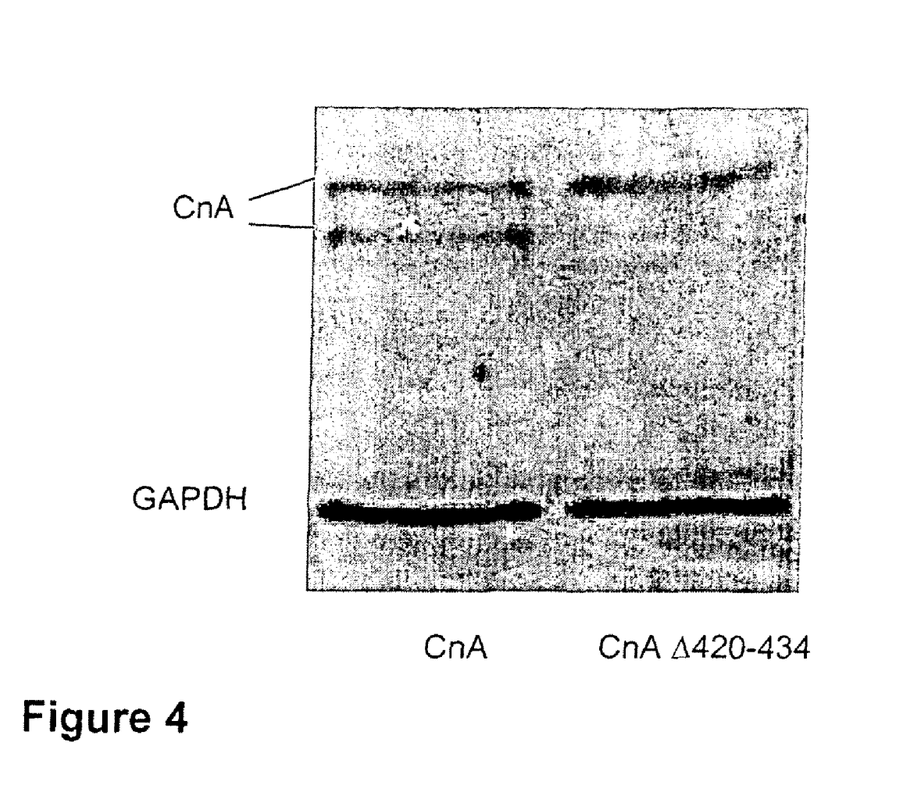
FIG. 4 shows nuclear export signals (NES) in calcineurin (CnA). CnA lacking the NES (Δ420-434) was resistant to proteolysis by calpain. GFP-tagged full length CnA and CnA (Δ420-434) were transfected into HeLa cells. Whole cell lysates were incubated with calpain I for 30 min and the lysates run on a 5% gel. Western blot analysis for GFP revealed proteolysis of full length CnA.

As different cleavage sites in the calcineurin sequence (Wu et al., 2004) have been described for calpain, the inventor assessed whether the NES sequence (423-434) really contains the calpain cleavage site. Therefore, the GFP-tagged calcineurin mutant lacking the NES domain was used for further experiments. The plasmid was transfected into HeLa cells and lysates of these cells expressing this deletion variant were incubated with calpain I. Western Blot analysis was used to demonstrate that full length CnA is proteolysed by calpain whereas CnAΔ423-434 is resistant to calpain mediated proteolysis (FIG. 4).

Mechanism of Nuclear Export of Calcineurin

A number of proteins that shuttle across the nuclear membrane have been identified using CRM1 as the export shuttle. Some are transcription factors like NF-ATc that confer pro-hypertrophic actions. Others act within counter-regulatory pathways that repress cardiac hypertrophic growth such as the transcriptional repressor HDAC5 (McKinsey et al., 2000). To address whether CnA nuclear export is mediated by CRM1, experiments using the CRM1 specific inhibitor, leptomycin B (LMB), were performed. Agonist-dependent nuclear import of full length CnA was achieved by Ang II stimulation. Calpeptin was added to prevent proteolysis of CnA. The addition of LMB to prevent CRM 1 mediated export indeed suppressed nuclear export of CnA. Together, these findings demonstrate that LMB confines CnA to the nucleus in the cardiomyocyte by blocking its nuclear export. This supports the hypothesis that nucleo-cytoplasmic shuttling of CnA is coupled to a NES between amino acids 423-434 and is mediated by CRM1.

Nuclear Accumulation of Calcineurin

In vivo studies of pathological myocardial hypertrophy showed that proteolysis of the calcineurin auto-inhibitory domain at amino acid 424 results in a constitutively active calcineurin mutant lacking both the AID (aa 468-490) and the NES (423-434). To determine whether loss of the AID or disruption of the NES is responsible for strong nuclear accumulation of CnA the nuclear import and export qualities of a GFP tagged CnA mutant with a deletion of the NES was investigated. Cells were transfected with CnAΔ423-434. In this case calcineurin resided in the cytosol. Stimulation of the transfected cells with Ang II resulted in subsequent translocation of CnA into the nucleus. Based on these results the inventor concluded that the AID not only blocks the catalytical activity of CnA but also masks the NLS. Removal of the AID via a conformational change in calcineurin following $Ca^{++}$ activation or by proteolysis of the auto-inhibitory domain leads to exposure of the NLS and resultant nuclear translocation of CnA.

Subsequent removal of the stimulating Ang II agent from the medium resulted in the CnAΔ423-434 mutant remaining nuclear, as the lack of the NES made it impossible for CRM1 to interact with CnA and to transport it back to the cytosol. The loss of the C-terminal part of CnA would therefore appear to regulate nuclear shuttling of CnA at the level of both nuclear import and export. Deprivation of the AID promotes import via importin β1, and loss of the NES hinders nuclear export via CRM1 mediated mechanisms.

A peptide corresponding to the calcineurin NLS inhibited CnA nuclear import and maintained the overall structure of CnA. The suppression of calcineurin transport into the nucleus is important for the NF-ATc transactivational status; this peptide is therefore useful as a tool to suppress myocardial hypertrophy.

Markers for Myocardial Hypertrophy

Figure 5A:
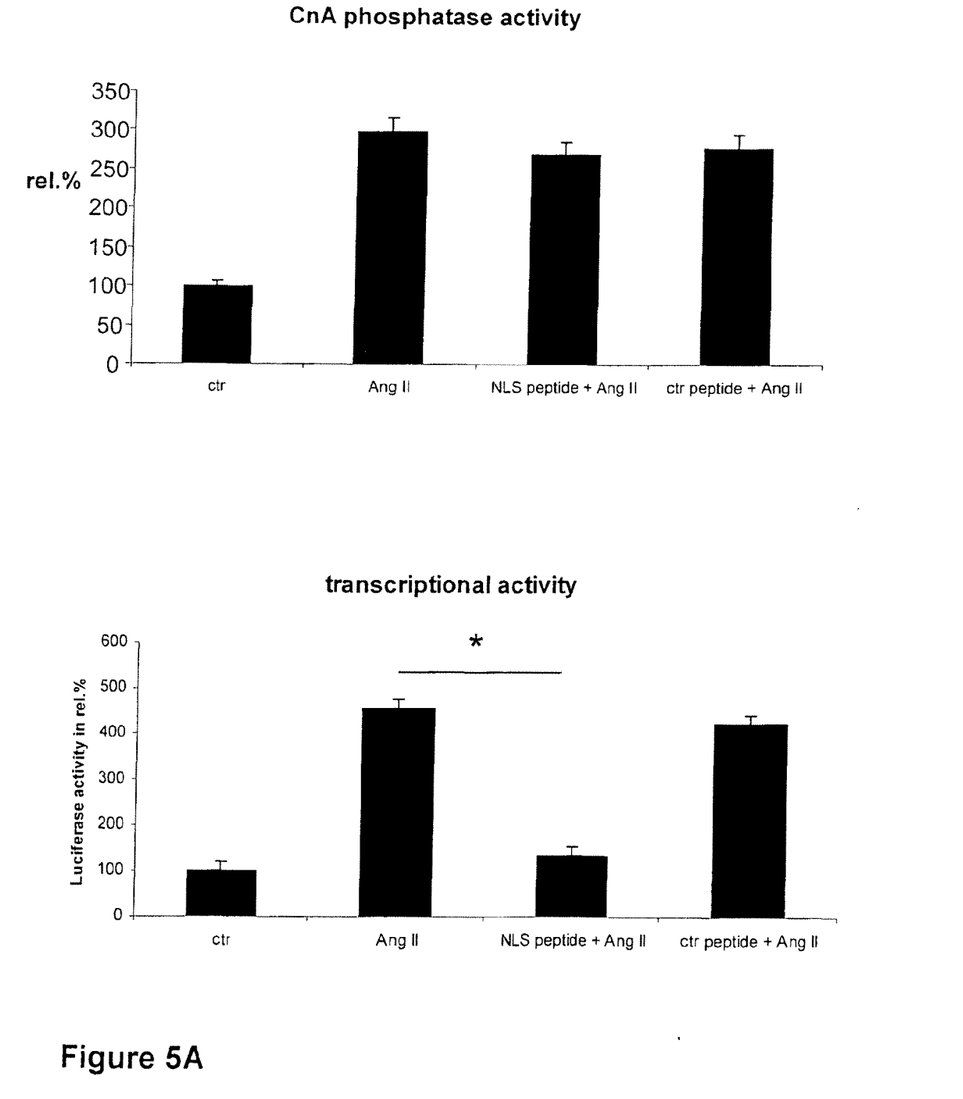
Figure 5B:
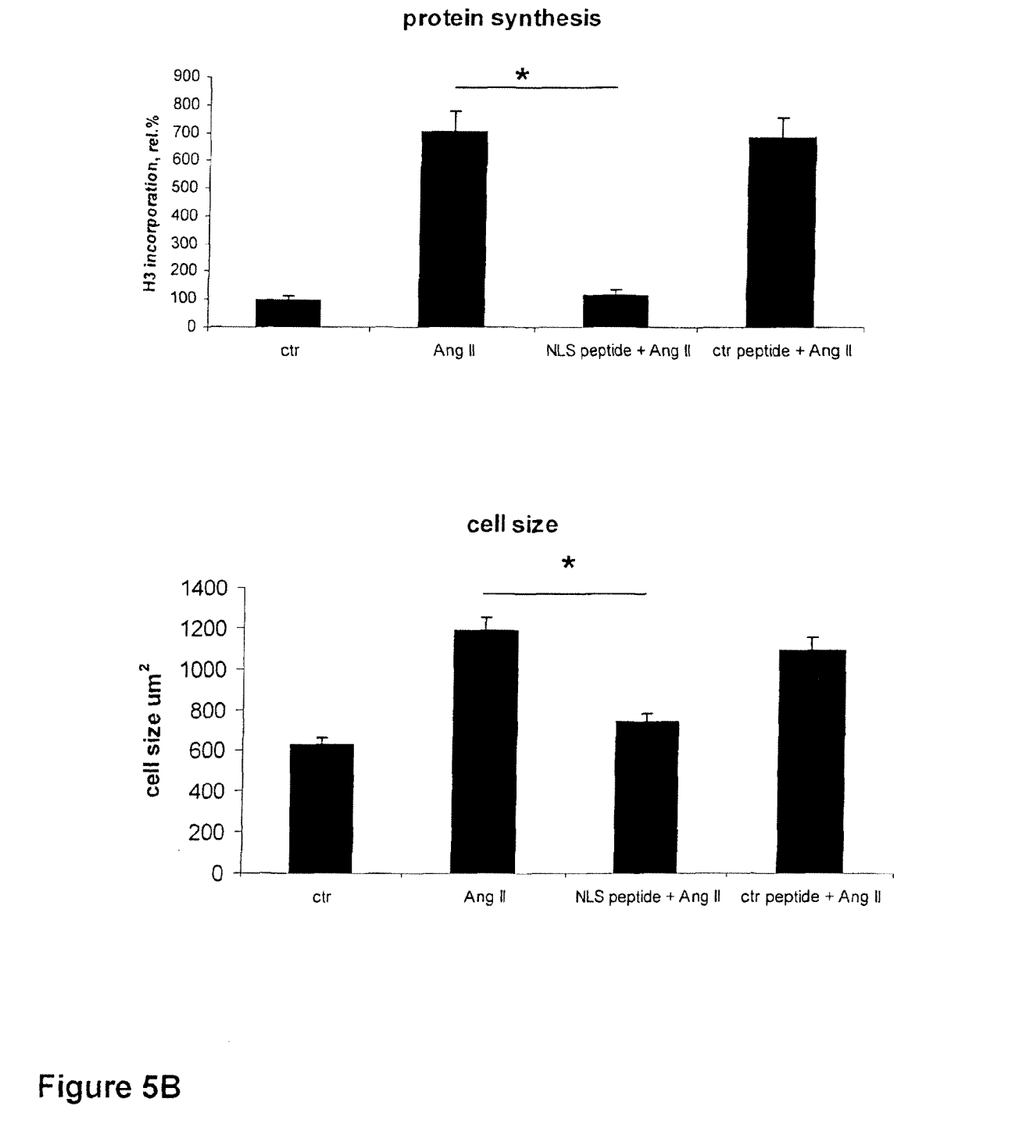
FIG. 5B shows that the development of myocardial hypertrophy was also suppressed by the inhibitory NLS peptide (SEQ ID NO: 2) as demonstrated by protein synthesis (FIG. 5B top) and cell size (magnification 600×) (FIG. 5B bottom).
Figure 5C:
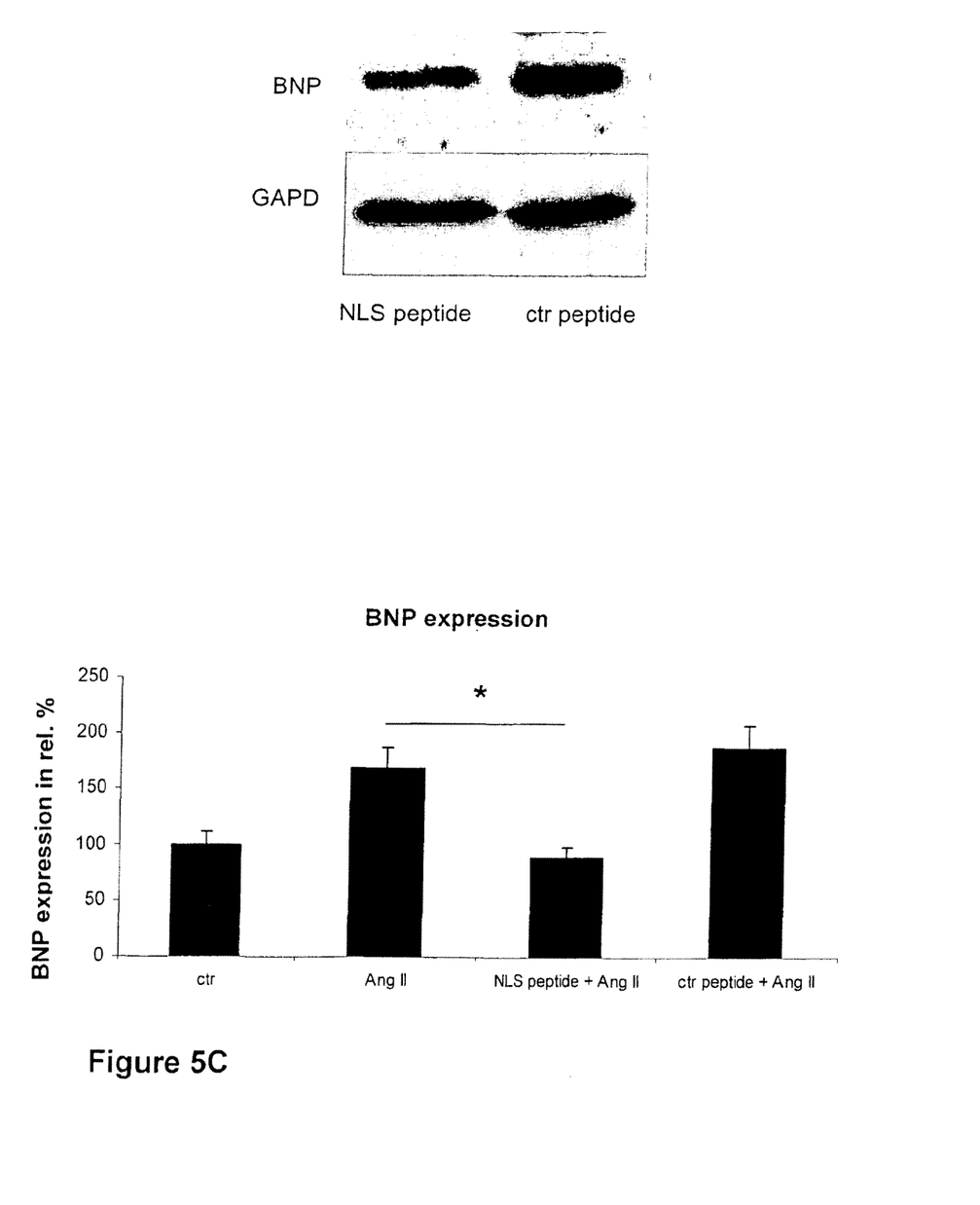
FIG. 5C shows that B-type natriuretic peptide (BNP), a molecular marker of hypertrophy, is suppressed by the use of the inhibitory NLS peptide (SEQ ID NO: 2).
Figure 5D:
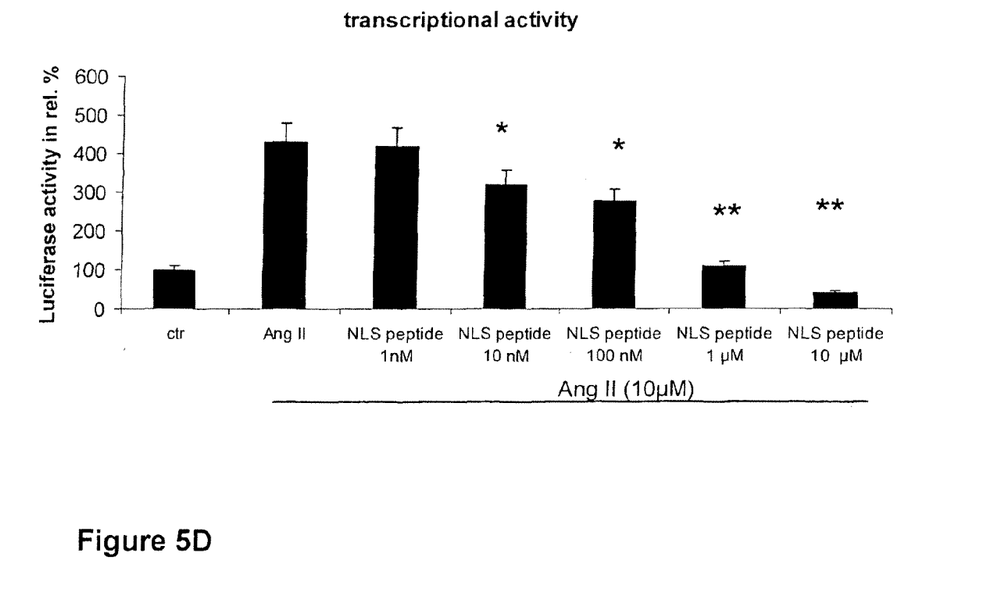
FIG. 5D shows the dose dependent decrease of NF-ATc transcriptional activity when treated with the NLS peptide of SEQ ID NO: 2. At higher concentrations (>1 μM, indicated by asterisk) a toxic effect is possible since values are below background levels of untreated cardiomyocytes (ctr=control).

Phosphatase activity, transcriptional activity, protein synthesis, cell size and makers of myocardial hypertrophy in response to the peptide related inhibition of CnA nuclear import were examined. Phosphatase activity was assessed employing a specific substrate (RII) for can (Ritter et al., 2002). Cardiomyocytes were stimulated with Ang II (10 μM), and CnA phosphatase activity was measured in the presence of the NLS peptide or a non sense control peptide. Total CnA phosphatase activity was not affected by inhibition of the access of importin β1 to the CnA NLS (289±17% vs. 273±11%, n=8, p=not significant). In contrast, transcriptional activity of the CnA/NF-ATc signalling pathway was decreased significantly by the NLS peptide (463±11% vs. 123±8%, n=8, p<0.05) (FIG. 5A top). Similarly, myocardial hypertrophy, as evidenced by protein synthesis (707±21% vs. 133±12%, n=8, p<0.05), cell size (1191±91 μm² vs. 728±65 μm², n=8, p<0.05) (FIG. 5B), and expression of brain natriuretic peptide (BNP) (163±11% vs. 88±8%, n=8, p<0.05) (FIG. 5C), were suppressed by the NLS peptide. Transcriptional activity of a NF-ATc luciferase reporter plasmid was decreased when nuclear import of CnA was blocked by the NLS peptide in a dose dependent manner (FIG. 5D).

These data indicated that despite full CnA phosphatase activity, CnA was unable to form effective transcriptional complexes. Activated calcineurin in itself does not appear to be sufficient to induce hypertrophy. Full transcriptional activity of CnA/NF-ATc is only possible in the presence of nuclear calcineurin. It is thus clear that calcineurin nuclear translocation is a prerequisite to the formation of effective NF-ATc transcriptional complexes.

T-Cell Experiments

The inventor above presented evidence, that inhibition of the interaction of the phosphatase calcineurin and its importin (importin β1) prevents nuclear translocation of calcineurin. This suppressed activation of the calcineurin/NF-AT signalling cascade (Hallhuber et al.). The above experiments were performed in cell cultures of isolated cardiomyocytes or immortalized cell lines.

Figure 6:
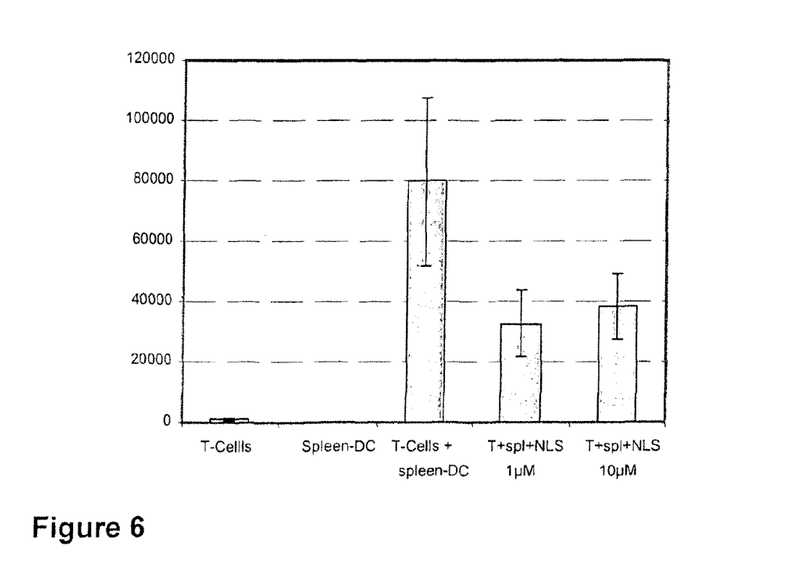
FIG. 6 shows T cells, which were stimulated with spleen dendritic cells as antigen stimulus. Bars indicate protein synthesis (H3-thymidin incorporation). When T cells were stimulated (spleen-DC) and simultaneously treated with the blocking peptide (NLS), protein synthesis was inhibited significantly.

The inventor now extended the experiments to T-cells and to in vivo experiments in mice. In FIG. 6 the inventor demonstrates suppression of T-cell function using the specific approach of competitive peptide inhibition of the calcineurin/importin interaction. The blocking peptide significantly prevented activation of lymphocytes.

Figure 7A:
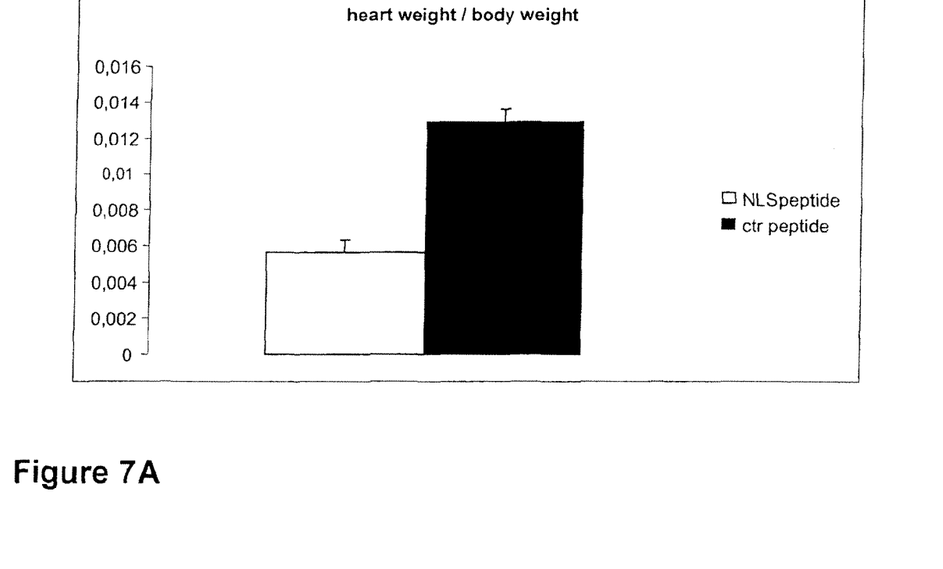
FIG. 7A shows the blocking peptide (NLS), which prevented an increase in heart weight in mice that were treated with Ang II for 4 weeks.
Figure 7B:
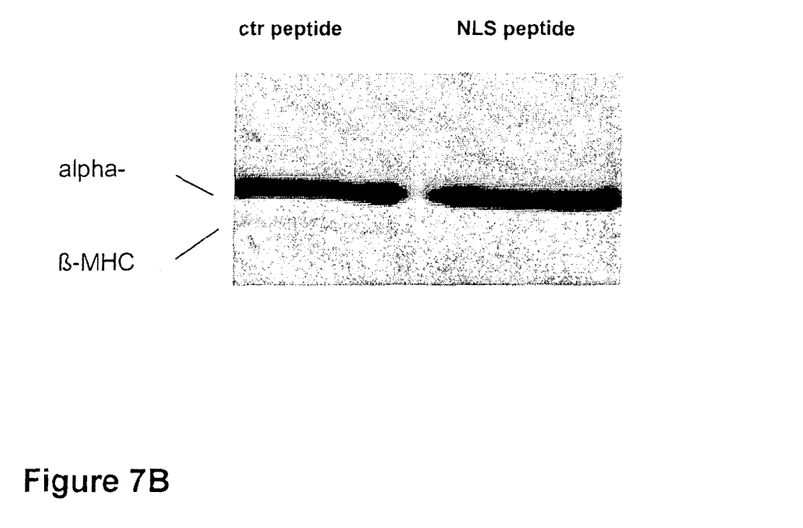
FIG. 7B shows the treatment of mice with the hypertrophic stimulus angiotensin for 4 weeks resulted in an upregulation of f-MHC as molecular marker of hypertrophy. The NLS peptide was able to suppress the development of myocardial hypertrophy in vivo and therefore prevented expression of this marker.

In FIG. 7 the inventor demonstrates in vivo data. For in vivo use the blocking peptide, that mimics the calcineurin nuclear localization signal (NLS) received a peptide extension to increase membrane permeability and was synthesised as a cyclic peptide to withstand proteolysis of N- and C-terminal proteases. This peptide was administered twice daily at a concentration of 25 mg/kg body weight/day by i.p. injections into mice. The mice were treated with implanted osmotic minipumps to release either angiotensin II or saline as control. Angiotensin II caused myocardial hypertrophy as demonstrated by the heart/body weight ratio and expression of molecular markers of hypertrophy. The blocking peptide was able to prevent the development of myocardial hypertrophy. On a cellular level the inventor could also demonstrate, that the blocking peptide suppressed calcineurin entry into the nucleus in vivo.

Similar results were seen in NFAT Luciferase reporter transgenic mice (mice were received from Wilkins et al. for the experiments). Administration of the NLS peptide in angiotensin II treated mice suppressed Luciferase activity and therefore demonstrated effectiveness of the NLS peptide in this animal model.

From the presented data it is concluded that inhibition of calcineurin/importin interaction and the resulting inhibition of calcineurin nuclear entry is a promising concept to inhibit the calcineurin/NF-AT signalling pathway. For the first time in vivo data and proof of concept in lymphocytes is provided. The NLS peptide can be used as therapeutic tool in further pathological conditions were suppression of calcineurin signalling is promising like treatment of myocardial hypertrophy, immunosuppression in rheumatic disease or in organ transplantation to suppress donor organ rejection. Additional therapeutic fields are psoriasis, colitis, allergic diseases as asthma or restenosis of coronary vessels after percutaneous interventions.

Further Alternative Nuclear Localization Signals and Membrane Ankers

Above evidence is presented that inhibition of the interaction of the phosphatase calcineurin and its importin (importin β1) prevents nuclear translocation of calcineurin. This suppressed activation of the calcineurin/NF-AT signalling cascade (Hallhuber et al. 2006). Previous experiments were performed in cell cultures of isolated cardiomyocytes or immortalized cell lines.

Figure 8:
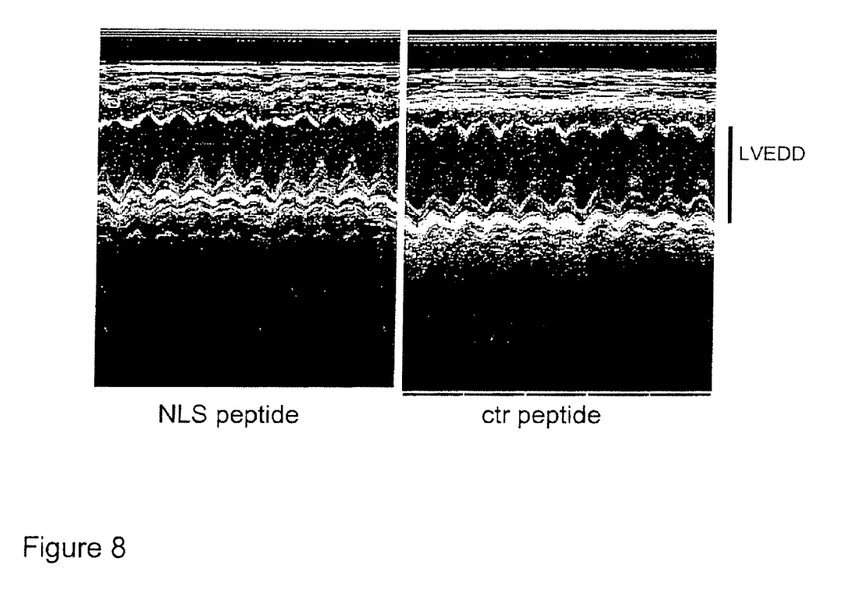
FIG. 8 shows the treatment of mice with implanted mini-osmotic pumps with AngII. This treatment caused dilation of the left ventricle (left ventricular end diastolic diameter, LVEDD). When the mice were treated with the NLS peptide dilation could prevented. A control peptide did not prevent left ventricular dilation.

The inventor now extended his experiments to in vivo data. Specifically, the inventor was able to show that the blocking peptide prevents myocardial hypertrophy in AngII treated mice as demonstrated by echocardiography (FIG. 8).

Figure 9:
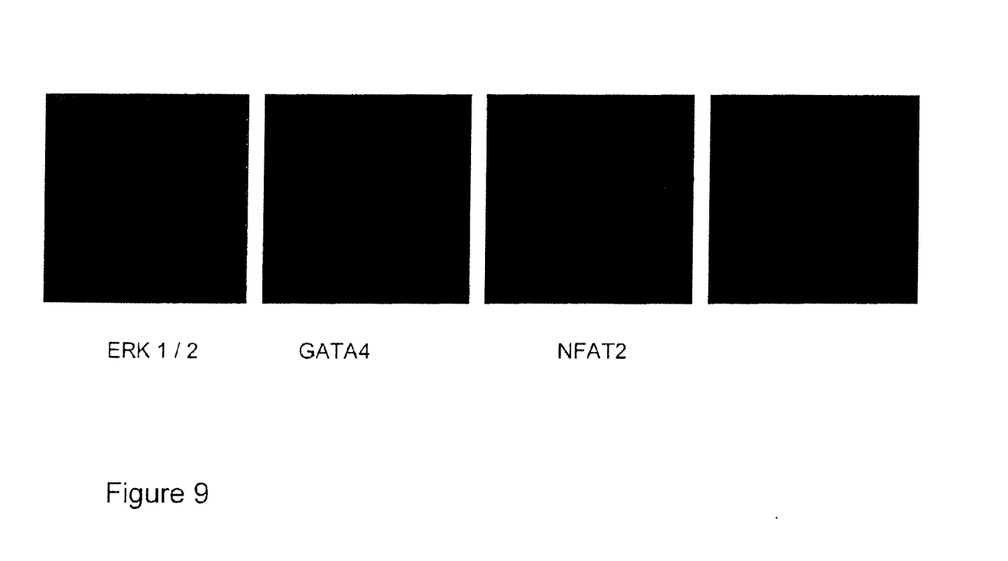
FIG. 9 shows the blocking peptide (NLS), which did not prevent nuclear accumulation of selected transcription factors (cJUN, ERK 1/2, GATA4, NFAT2) in cardiomyocytes that were stimulated with phenylephrin.

The inventor also analyzed the specificity with the peptide (AAVALLPAVLAALAA KQECKIKYSERV SEQ ID NO:

5). In theory this peptide that mimics the Calcineurin NLS saturates the binding site on importin and therefore might completely block importin function for other transcription factors as well. However, this peptide did not block import of selected transcription factors, that also utilize importin β3 (such as cJun, GATA4, NFAT2 and ERH 1/2) (FIG. 9).

The inventor also tested different amino acid sequences that are theoretically more resistant to proteolysis for the capacity to inhibit calcineurin/importin interaction, namely:

| | | |
|---|---|---|
| AAVALLPAVLAALAA KQEAKIKYSERV | (SEQ ID NO: 6) | |
| AAVALLPAVLAALAA KQECKIKYAERV | (SEQ ID NO: 7) | |
| AAVALLRAVLAALAA KQEAKIKYAERV | (SEQ ID NO: 8) | |
| AAVALLPAVLAALAA KAECKIKYSERV | (SEQ ID NO: 9) | |
| AAVALLPAVLAALAA KAEAKIKYSERV | (SEQ ID NO: 10) | |

These peptides have all the same impact: they do block calcineurin/importin interaction as demonstrated in coimmunoprecipitation experiments

CONCLUSION

The inventor's data show that CRM1 not only exports NF-ATc, but also calcineurin across the nuclear envelope. To interrupt transcriptional activity of the calcineurin/NF-ATc signalling cascade CRM1 is first required to export calcineurin, so that in a second round CRM1 can access the NES of NF-ATc and subsequently proceed with its nuclear export. This mechanism is prevented in myocardial hypertrophy by the proteolysis of calcineurin by calpain at amino acid 424, resulting in loss of the auto-inhibitory domain including the NES. In this scenario calcineurin remains nuclear because it is inaccessible to the export protein CRM1.

As import always precedes export, the inhibition of CnA nuclear import by peptide competition for the binding of the nuclear import protein importin β1 presents a more sophisticated approach to abolishing the deleterious effects of exaggerated NF-ATc transcriptional activity. Therefore the NLS peptide is useful as a new therapeutic agent for pathologic myocardial hypertrophy.

REFERENCES

1. Burkard, N. et al. Targeted proteolysis sustains calcineurin activation. Circulation 111, 1045-53 (2005).
2. Cyert, M. S. Regulation of nuclear localization during signaling. J Biol Chem 276, 20805-8 (2001).
3. Dolmetsch, R. E., Lewis, R. S., Goodnow, C. C. & Healy, J. I. Differential activation of transcription factors induced by $Ca^{2+}$ response amplitude and duration. Nature 386, 855-8 (1997).
4. Fornerod, M., Ohno, M., Yoshida, M. & Mattaj, I. W. CRM1 is an export receptor for leucine-rich nuclear export signals. Cell 90, 1051-60 (1997).
5. Frey, N., Richardson, J. A. & Olson, E. N. Calsarcins, a novel family of sarcomeric calcineurin-binding proteins. Proc Natl Acad Sci USA 97, 14632-7 (2000).
6. Hallhuber M, Burkard N, Wu R. Buch M H, Engelhardt S, Hein L, Neyses L, Schuh K, Ritter O. Inhibition of nuclear import of calcineurin prevents myocardial hypertrophy. Circ Res. 2006; 99:626-35
7. Hogan, P. G. & Rao, A. Transcriptional regulation. Modification by nuclear export? Nature 398, 200-1. (1999).

8. Jans, D. A., Xiao, C. Y. & Lam, M. H. Nuclear targeting signal recognition: a key control point in nuclear transport? Bioessays 22, 532-44 (2000).
9. Kutay, U., Bischoff, F. R., Kostka, S., Kraft, R. & Gorlich, D. Export of importin alpha from the nucleus is mediated by a specific nuclear transport factor. Cell 90, 1061-71 (1997).
10. McKinsey, T. A., Zhang, C. L., Lu, J. & Olson, E. N. Signal-dependent nuclear export of a histone deacetylase regulates muscle differentiation. Nature 408, 106-11 (2000).
11. Pemberton, L. F. & Paschal, B. M. Mechanisms of receptor-mediated nuclear import and nuclear export. Traffic 6, 187-98 (2005).
12. Ritter, O. et al. Calcineurin in human heart hypertrophy. Circulation 105, 2265-9. (2002).
13. Ritter, O. et al. AT2 receptor activation regulates myocardial eNOS expression via the calcineurin-NF-AT pathway. Faseb J 17, 283-5. (2003).
14. Shibasaki, F., Price, E. R., Milan, D. & McKeon, F. Role of kinases and the phosphatase calcineurin in the nuclear shuttling of transcription factor NF-AT4. Nature 382, 370-3. (1996).
15. Timmerman, L. A., Clipstone, N. A., Ho, S, N., Northrop, J. P. & Crabtree, G. R. Rapid shuttling of NF-AT in discrimination of $Ca^{2+}$ signals and immunosuppression. Nature 383, 837-40. (1996).
16. Wilkins B J, Dai Y S, Bueno O F, Parsons S A, Xu J, Plank D M, Jones F, Kimball T R, Molkentin J D. Calcineurin/NFAT coupling participates in pathological, but not physiological, cardiac hypertrophy. Circ Res. 2004; 94:110-8.
17. Wu, H. Y. et al, Critical role of calpain-mediated cleavage of calcineurin in excitotoxic neurodegeneration. J Biol Chem 279, 4929-40 (2004).
18. Zhu, J. & McKeon, F. NF-AT activation requires suppression of Crm1-dependent export by calcineurin. Nature 398, 256-60. (1999).
19. Zou, Y. et al. Isoproterenol activates extracellular signal-regulated protein kinases in cardiomyocytes through calcineurin. Circulation 104, 102-8 (2001).

The invention claimed is:

1. A kit comprising the peptide of SEQ ID NO: 1, 2, 5-9 or 10.

2. A therapeutic agent comprising the peptide of SEQ ID NO: 1, 2, 5-9 or 10.

3. An agent comprising a nucleic acid which encodes the peptide of SEQ ID NO: 1, 2, 5-9 or 10.

4. A therapeutic agent comprising a peptide of at least 90% identity of the peptide of SEQ ID NO: 1, 2, 5-9 or 10; wherein the peptide substantially inhibits the translocation of calcineurin from the cytoplasm to the nucleus of a cell.

5. The therapeutic agent of claim 2, further comprising a pharmaceutically acceptable carrier.

6. An antibody that specifically binds the peptide of SEQ ID NO: 1, 2, 5-9 or 10.

7. A peptide consisting of the amino acid sequence of SEQ ID NO: 1, 2, 5-9, or 10.

8. A therapeutic agent comprising a peptide of at least 95% identity of the peptide of SEQ ID NO: 1, 2, 5-9 or 10; wherein the peptide substantially inhibits the translocation of calcineurin from the cytoplasm to the nucleus of a cell.

9. A therapeutic agent comprising a peptide of at least 98% identity of the peptide of SEQ ID NO: 1, 2, 5-9 or 10; wherein the peptide substantially inhibits the translocation of calcineurin from the cytoplasm to the nucleus of a cell.

10. A therapeutic agent comprising a peptide of 100% identity of the peptide of SEQ ID NO: 1, 2, 5-9 or 10; wherein the peptide substantially inhibits the translocation of calcineurin from the cytoplasm to the nucleus of a cell.

11. The agent of claim 3, further comprising a pharmaceutically acceptable carrier.

12. The therapeutic agent of claim 4, further comprising a pharmaceutically acceptable carrier.

* * * * *